United States Patent [19]

Onoda et al.

[11] 4,041,082

[45] Aug. 9, 1977

[54] PROCESS FOR PRODUCING ALDEHYDES

[75] Inventors: Takeru Onoda, Yokohama; Tetsuo Masuyama, Machida, both of Japan

[73] Assignee: Mitsubishi Chemical Industries Limited, Tokyo, Japan

[21] Appl. No.: 599,198

[22] Filed: July 25, 1975

[30] Foreign Application Priority Data

July 25, 1974  Japan .................................. 49-85523

[51] Int. Cl.$^2$ ............................................ C07C 45/08
[52] U.S. Cl. ............................................. 260/604 HF
[58] Field of Search ............................... 260/604 HF

[56] References Cited

U.S. PATENT DOCUMENTS 3,239,566   3/1966   Slaugh ............................ 260/604 R
3,527,809   9/1970   Pruett et al. ..................... 260/604 R

*Primary Examiner*—James O. Thomas, Jr.
*Assistant Examiner*—W. B. Lone
*Attorney, Agent, or Firm*—Sughrue, Rothwell, Mion, Zinn and Macpeak

[57] ABSTRACT

In a process for producing an aldehyde by hydroformylation comprising reacting an olefin with carbon monoxide and hydrogen in the presence of a solution of a rhodium-tertiary phosphine complex catalyst and recycling the catalyst-containing solution to the reaction zone after recovering the aldehyde formed by distillation in a distillation zone, the catalyst inactivated by the hydroformylation is reactivated effectively by treating the catalyst-containing solution with carbon dioxide.

18 Claims, No Drawings

PROCESS FOR PRODUCING ALDEHYDES

BACKGROUND OF THE INVENTION

1. Field of the Invention

The present invention relates to a process of producing aldehydes and, more particularly, it relates to a process of producing aldehydes by hydroformylating olefins in the presence of a rhodium-tertiary phosphine complex catalyst while maintaining the catalytic activity at a high level.

2. Description of the Prior Art

Recently, the hydroformylation of olefins using a soluble rhodium complex catalyst containing a tertiary phosphine as at least one of the ligands (hereinafter, for simplicity, the catalyst is referred to as a rhodium-tertiary phosphine complex catalyst) has been developed (e.g., as disclosed in U.S. Pat. No. 3,527,809), since the catalyst possesses a high catalytic activity, a quite high selectivity for aldehydes, in particular, for more valuable straight-chain aldehydes in the hydroformylation reaction of $\alpha$-olefins, and a high stability which makes it possible to carry out the reaction under reduced pressure.

A rhodium-tertiary phosphine complex catalyst has an important advantage because of its high stability in that after separating the aldehyde thus formed the reaction product solution by distillation, the residual solution containing the rhodium-tertiary phosphine complex catalyst can be recycled to the reaction zone as a catalyst solution.

However, in the course of the repeated use of the recycled catalyst solution, high-boiling by-products and complexes which do not have any or have a reduced catalytic activity formed by a change in the structure of the rhodium-tertiary phosphine complex catalyst itself and by the action of impurities such as oxygen, halogens, sulfur, etc., contained to a small extent in the starting materials accumulate gradually in the catalyst solution.

Therefore, in order to carry out the hydroformylation reaction continuously and in a stable manner, a technique where the catalytic activity of the recyclic catalyst solution is maintained at a constant level by supplying fresh catalyst to the recycled solution and at the same time removing a part of the recycled catalyst solution must be employed.

In this case, however, recovery of rhodium from the catalyst solution thus removed from the recycling system is inevitable since rhodium is a quite expensive metal. However, the operation of recovering rhodium from the solution is complicated and this makes the hydroformylation reaction economically disadvantageous.

SUMMARY OF THE INVENTION

An object of this invention is, therefore, to provide an industrially advantageous process for producing aldehydes.

Another object of this invention is to provide a process for producing aldehydes in which the need for employing a complicated process for recovering rhodium from the recycled catalyst solution is eliminated.

Still another object of this invention is to provide an effective process for reactivating the rhodium-tertiary phosphine complex catalyst inactivated in the course of the recycled use of the catalyst solution in the production of aldehydes by the hydroformylation of olefins.

As the result of investigations on processes for restoring the activity of the catalyst inactivated in the recycle system of a hydroformylation reaction to reduce the burden of recovering the rhodium from a catalyst solution containing the inactivated catalyst, it has now been discovered that the inactivated catalyst can be remarkably reactivated by treating the catalyst solution containing the inactivated catalyst with carbon dioxide.

That is, in a process for producing an aldehyde comprising the steps of supplying an olefin, carbon monoxide, and hydrogen to a hydroformylation reaction zone together with a catalyst solution containing a rhodium-tertiary phosphine complex catalyst dissolved in a solvent to form therein an aldehyde, separating the aldehyde from the catalyst solution by distilling the reaction mixture containing the aldehyde from the hydroformylation reaction zone in a distillation zone, and recycling the catalyst solution obtained from the distillation zone to the hydroformylation reaction zone, the improvement which comprises contacting the catalyst solution with carbon dioxide in the hydroformylation reaction zone or in the recycling system of the catalyst solution.

DETAILED DESCRIPTION OF THE INVENTION

As described above, the invention is concerned with a process for reactivating a rhodium-tertiary phosphine complex catalyst inactivated in the hydroformylation reaction of olefins for producing aldehydes.

Rhodium-tertiary phosphine complex catalysts are known, e.g., as disclosed in U.S. Pat. Nos. 3,239,566 and 3,527,809, and various kinds of tertiary phosphines and other ligands, various forms of the catalysts, and various processes of preparing such catalysts have been proposed. Furthermore, various reaction conditions have been reported for the hydroformylation reactions of olefins using rhodium-tertiary phosphine complex catalysts. In general, the hydroformylation reaction is carried out under a low pressure utilizing the characteristics that the complexes are stable. The reaction temperature is usually about 50° to 200° C., preferably 60° to 150° C., and the molar feed ratio of hydrogen to carbon monoxide ($H_2$:CO) employed in the reaction is usually about 1:3 to 7:1.

The hydroformylation reaction employed in this invention is usually carried out in an inert solvent and in this case, solvents having higher boiling points than the boiling points of the aldehydes formed in the reaction are preferred for use. The use of such a solvent facilitates the recycle of the catalyst. That is, in using the solvent, by distilling the reaction mixture obtained from the reaction zone, an aldehyde-containing fraction and a solvent fraction containing the rhodium-tertiary phosphine complex catalyst dissolved therein can be separately recovered and the solvent fraction containing the catalyst can be recycled into the reaction zone. Suitable examples of the olefins which can be used as a starting material in the hydroformylation reaction of this invention include aliphatic olefins such as ethylene, propylene, butene, hexene and the like, and alicyclic olefins such as cyclopentane, cyclohexane and the like, or olefinic compounds in which these olefins are substituted with substituents inert to the hydroformylation reaction of this invention. For example, in the hydroformylation reaction of propylene, an aromatic hydrocarbon such as toluene, xylene, etc., a saturated aliphatic hydrocarbon such as decane, etc., and an alcohol such as butanol are preferably used. If desired, the aldehyde which is the reaction product in the hydroformylation reaction can be also used as the solvent.

As the rhodium-tertiary phosphine complex catalyst, a pre-prepared complex, such as hydridocarbonyl tris(-triphenylphosphine)rhodium, etc. can be used. Alternatively, a readily available rhodium compound, i.e., an organic acid salt of rhodium, such as rhodium acetate, etc., and an inorganic acid salt of rhodium, such as rhodium nitrate, rhodium sulfate, etc., is introduced into the reaction zone as a solution in an appropriate solvent together with a tertiary phosphine to form in situ a complex of rhodium and the tertiary phosphine in the reaction zone in the presence of a mixed gas of carbon monoxide and hydrogen (hereinafter, this gas mixture is referred to as "oxo gas").

The concentration of the rhodium-tertiary phosphine complex catalyst in the reaction solvent in the reaction zone can vary widely but the concentration usually ranges from about 0.1 mg. to 500 mg., preferably from 1 mg. to 100 mg., per liter of the solvent calculated as atomic rhodium (the concentration being at normal temperature and normal pressure). Preferably, however, a solution of the catalyst having as low a rhodium concentration as possible is used since rhodium is quite expensive. In the hydroformylation reaction of propylene which is one of the most important industrial applications of the hydroformylation reaction, the reaction can be carried out using a catalyst solution having a concentration of from about 1 mg. to 50 mg. per liter of the solvent by suppressing the deactivation of the catalyst using the oxo gas and propylene each containing a low proportion of impurities such as sulfur, chlorine, acetylene, dienes, etc.

Although the exact form the rhodium-tertiary phosphine complex reactive to the hydroformylation reaction possesses has not yet been clarified, the complex is believed to be in a form wherein the tertiary phosphine, carbon monoxide, hydrogen, and further an olefin are coordinated with the rhodium. It is further believed that in this case the active complex is not in a definite form but is in an equilibrium between complexforms having different ligands depending on the competitive coordination of each ligand and the equilibrium varies due to changes in the concentration of each ligand.

Upon coordination with rhodium, the phosphine contributes to increase the stability of the complex and in order to provide a stable complex catalyst capable of being repeatedly used for the hydroformylation reaction of olefins, the tertiary phosphine preferably is present in the complex in a proportion of more than about 5 moles per gram atom of rhodium and a complex containing 5 to 200 moles of tertiary phosphine per gram atom of rhodium is usually used.

Various tertiary phosphines including triarylphosphines and trialkylphosphines can be used in this invention but in general the use of triarylphosphines, in particular, triphenylphosphines are preferred.

The concentration of the phosphine in the complex catalyst influences the ratio ($n/i$) of straight chain isomer to branched chain isomer of the aldehyde produced and, for example, in the hydroformylation of propylene, the $n/i$ ratio tends to increase as the concentration of the tertiary phosphine increases. However, since tertiary phosphines are also expensive, the use of a complex catalyst having a high concentration of the phosphine is economically disadvantageous. Accordingly, in the hydroformylation of propylene, it is advantageous to carry out the reaction at an oxo gas partial pressure of about 30 to 100 kg/cm.$^2$ using a complex catalyst having a tertiary phosphine concentration of about 1 to 30 m. mole per liter of solvent by considering the relationship of the oxo gas partial pressure, the concentration of the tertiary phosphine, and the ratio ($n/i$) of the aldehyde isomers produced.

Examples of techniques of bringing the recycling catalyst solution containing the inactivated rhodium-tertiary phosphine complex catalyst according to this invention include a method in which carbon dioxide is added to the oxo gas in the reaction zone for the hydroformylation to simultaneously contact the catalyst solution with carbon dioxide and the hydroformylation reaction in the same reaction zone, a method in which the hydroformylation reaction is temporarily interrupted and only the catalyst solution and carbon dioxide are introduced to the reaction zone to contact the catalyst solution and the carbon dioxide, and further a method in which, after separating the aldehyde formed from the reaction mixture obtained from the hydroformylation reaction, the residual catalyst solution is partially or completely contacted with carbon dioxide prior to recycling in a carbon dioxide treatment chamber separately installed and then recycled into the reaction zone. The contact of the catalyst solution with carbon dioxide can be either in a continuous manner or a batch manner, and is, in general, carried out by bubbling the carbon dioxide into a bubbling tower or an agitation tank. In contacting the catalyst solution with the carbon dioxide, the contact period of time can be reduced with increased partial pressure of the carbon dioxide and higher temperatures for the treatment.

Usually, the partial pressure of carbon dioxide employed is higher than about 1 kg./cm$^2$, preferably about 5 to 100 kg/cm.$^2$ and the contact temperature is appropriately selected in a range of about 60° to 200° C. The contact period of time can be changed appropriately according to the partial pressure of the carbon dioxide and the contact temperature, but usually ranges from about 30 minutes to 5 hours. The carbon dioxide is added in a large excess amount to the rhodium, but the amount of carbon dioxide employed can vary.

Also, the carbon dioxide used need not be pure but can contain an inert gas such as nitrogen, etc., and the oxo gas.

According to the process of this invention, an olefin can be hydroformylated while maintaining the catalytic activity of the rhodium-tertiary phosphine complex catalyst at a high level. That is, by continuously bringing a part or all of the catalyst solution into contact with carbon dioxide, the rate of the reduction in the catalytic activity of the complex catalyst can be greatly reduced and also by intermittently bringing a part or all of the catalyst solution into contact with carbon dioxide, the catalytic activity of the inactivated catalyst can be regenerated.

In fact, a reduction in the catalytic activity is unavoidable to some extent if only the catalyst solution with carbon dioxide in the process of this invention is used and hence in the practice of this invention the rate of reaction in the hydroformylation is maintained at a constant value by, if desired, removing continuously or intermittently a portion of the recycled catalyst solution and supplying a fresh catalyst solution in an amount corresponding to the amount of the catalyst solution removed. Even in such case, however, the amount of the fresh catalyst solution supplied is greatly reduced as compared with the case where the treatment of the catalyst solution with carbon dioxide is omitted, which shows also the economical importance of the process of this invention.

The invention will be explained more specifically by reference to the following examples but the invention is not to be construed as being limited to these examples. Unless otherwise indicated herein, all parts, percents, ratios and the like are on a molar basis.

In addition, prior to the descriptions of the examples, the reaction rate constant in a batch reaction using a fresh catalyst was determined in the Reference Example shown below and the reduction of the catalytic activity of the catalyst solution by the repeated use thereof was confirmed in the Comparison Example.

REFERENCE EXAMPLE

In a 200 ml. autoclave equipped with an electromagnetic stirrer were charged 50 ml. of toluene, 63.5 mg. of triphenylphosphine, and 0.5 mg of rhodium acetate, calculated as atomic rhodium, and after purging the interior of the autoclave with argon gas, 250 m. mole of propylene was fed into the autoclave.

Then, the temperature of the autoclave was increased to 120° C. and an oxo gas having an $H_2:CO$ ratio of 1.17 was charged into the autoclave until the total pressure in the autoclave became 50 kg./cm$^2$ to initiate the reaction. The autoclave was connected to a gas bomb through a pressure-controlling means and the gas supplied to the autoclave for supplementing the gas consumed in the reaction to maintain the interior pressure of the autoclave constant during the reaction.

Since the degree of the reaction rate could be treated as almost zero degree to the concentration of propylene until the conversion of propylene reached 50% under the above described reaction conditions, the rate constant of the reaction $K_o$ was calculated from the reduction in pressure of the gas bomb.

When the gas absorption ceased, which was considered to indicate reaction completion, the autoclave was cooled, the unreacted propylene and butyraldehyde formed contained in the gaseous phase and the liquid phase were determined by gas chromatography. The results showed that the conversion of propylene was higher than 99% and the selectivity to butyraldehyde was higher than 98%. The results are also shown in Table 1 below.

COMPARISON EXAMPLE

In an 18 liter reaction vessel were introduced toluene, from which dissolved and adsorbed oxygen had previously been removed, propylene, and triphenylphosphine, at rates of 6 liters/hour, 30 moles/hour, and 24 m. moles/hour, respectively, together with rhodium acetate at a rate of 48 mg./hour, calculated as atomic rhodium and at the same time, an oxo gas having an $H_2:CO$ ratio of 1.1 was introduced into the reaction vessel at a rate of 1200 liter(STP)/hour, whereby the hydroformylation reaction of propylene was carried out at a reaction pressure of 50 kg./cm.$^2$ and a reaction temperature of 110° C. The reaction mixture obtained was subjected to a gas-liquid separation after cooling and the gaseous phase thus separated was recycled into the reaction vessel while the liquid phase was distilled to recover butyraldehyde, whereby a catalyst solution containing a rhodium-tertiary phosphine complex was obtained as the still residue.

Then, the catalyst solution thus obtained, the above-described propylene and oxo gas were fed into the reaction chamber indicated above at rates of 6 liters/hour, 30 moles/hour, and 1200 liter(STP)/hour, respectively, and the hydroformylation reaction of propylene was carried out under the same conditions as above.

The catalyst solution obtained by repeating the procedure 15 times was distilled to distil away a small amount of toluene, whereby the concentration of rhodium was adjusted to 10 mg/liter calculated as atomic rhodium. In this case the concentration of triphenylphosphine was 1.17 g./liter.

Propylene was fed into the autoclave as in the Reference Example and the hydroformylation reaction of propylene was carried out using 50 ml. of the catalyst solution thus obtained in the same manner as in the Reference Example. The results obtained are shown in Table 1 below.

EXAMPLE 1

In a 200 ml. autoclave equipped with an electromagnetic stirrer was charged 50 ml. of the catalyst solution having reduced activity obtained in Comparison Example and after introducing therein carbon dioxide, from which oxygen had been completely removed, the treatment of the catalyst solution with carbon dioxide was carried out for 2 hours at 20 kg./cm.$^2$ and at 120° C. After finishing the treatment with carbon dioxide, the gas in the autoclave was purged and propylene was fed into the autoclave to carry out the hydroformylation reaction under the same conditions as in the Reference Example. The results obtained are shown in Table 1 below.

EXAMPLE 2

The same procedure as in Example 1 was followed except that the pressure of carbon dioxide and the treatment period of time were changed to 40 kg./cm.$^2$ and one hour, respectively. The results obtained are shown in Table 1 below.

EXAMPLE 3

The same procedure as in the Reference Example was followed using 50 ml. of the catalyst solution having reduced activity obtained in the Comparison Example while changing the partial pressure of the carbon dioxide and the total pressure in the autoclave to 10 kg./cm.$^2$ and 60 kg./cm.$^2$, respectively. The results obtained are shown in Table 1 below.

EXAMPLE 4

The same procedure as in Example 3 was followed except that the partial pressure of carbon dioxide and the total pressure in the autoclave were changed to 20 kg./cm.$^2$ and 70 kg./cm.$^2$, respectively. The results obtained are shown in Table 1 below.

TABLE 1

| Example | Reaction Rate $K_o$ (mole/liter.hr.) | n/i of Butyraldehyde Produced |
| --- | --- | --- |
| Reference Example | 3.97 | 1.7 |
| Comparison Example | 2.17 | 1.6 |
| Example 1 | 2.91 | 1.7 |
| Example 2 | 2.74 | 1.7 |
| Example 3 | 2.68 | 1.7 |
| Example 4 | 2.91 | 1.7 |

What is claimed is:

1. In a process for producing an aldehyde including the steps of supplying to a hydroformylation reaction zone an olefin selected from the group consisting of ethylene, propylene, butene and hexene, carbon monoxide and hydrogen together with a catalyst solution consisting essentially of a solvent and a rhodium-tertiary phosphine complex catalyst dissolved therein to form an aldehyde, distilling the reaction mixture obtained from the hydroformylation reaction zone and containing the aldehyde formed in a distillation zone to separate the aldehyde from the catalyst solution, and recycling the catalyst solution from the distillation zone to the hydroformylation reaction zone, the improvement which comprises contacting at least a part of the catalyst solution with carbon dioxide having the partial pressure higher than about 1 Kg/cm$^2$ at a temperature of about 60° to 200° C in the hydroformylation reaction zone.

2. The process as claimed in claim 1, wherein the carbon dioxide partial pressure is about 1 to 100 Kg/cm$^2$.

3. The process as claimed in claim 1, wherein said tertiary phosphine of the complex catalyst is a triarylphosphine.

4. The process as claimed in claim 1, wherein said olefin is propylene.

5. The process as claimed in claim 1, wherein said olefin is ethylene.

6. The process as claimed in claim 1, wherein the molar ratio of hydrogen to carbon monoxide supplied to the hydroformylation reaction zone is about 1:3 to 7:1.

7. The process as claimed in claim 1, wherein the reaction temperature in the hydroformylation reaction zone is about 50° to 200° C.

8. The process as claimed in claim 1, wherein the concentration of the rhodium-tertiary phosphine complex in the catalyst solution supplied to the hydroformylation reaction zone is about 0.1 to 500 mg. per liter of the solvent calculated as atomic rhodium.

9. In a process of producing butyraldehyde including the steps of supplying propylene, carbon monoxide, and hydrogen to a hydroformylation reaction zone, the molar ratio of said hydrogen to said carbon monoxide ranging from about 1:3 to 7:1, together with a catalyst solution of a rhodium-triphenylphosphine complex having a rhodium concentration of about 1 to 100 mg. per liter of the solvent calculated as atomic rhodium and a triphenylphosphine concentration of about 1 to 30 m. moles per liter of the solvent and including about 5 to 200 moles of the triphenylphosphine per gram atom of rhodium to form butyraldehyde at a total pressure of carbon monoxide and hydrogen of about 30 to 100 kg/cm$^2$ and a reaction temperature of about 60° to 150° C., distilling the reaction mixture containing butyraldehyde obtained from the hydroformylation reaction zone in a distillation zone to separate butyraldehyde from the catalyst solution, and recycling the residual catalyst solution from the distillation zone to the hydroformylation reaction zone, the improvement which comprises contacting the catalyst solution with carbon dioxide at a partial pressure of carbon dioxide of about 5 to 100 kg/cm$^2$ and a temperature of about 60° to 200° C in the hydroformylation reaction zone.

10. In a process of producing butyraldehyde including the steps of supplying propylene, carbon monoxide, and hydrogen to a hydroformylation reaction zone, the molar ratio of said hydrogen to said carbon monoxide ranging from about 1:3 to 7:1, together with a catalyst solution of a rhodium-triphenylphospine complex having a rhodium concentration of about 1 to 100 mg. per liter of the solvent calculated as atomic rhodium and a triphenylphosphine concentration of about 1 to 30 m. moles per liter of the solvent and including about 5 to 200 moles of the triphenylphosphine per gram atom of rhodium to form butyraldehyde at a total pressure of carbon monoxide and hydrogen of about 30 to 100 kg/cm$^2$ and a reaction temperature of about 60° to 150° C, distilling the reaction mixture containing butyraldehyde obtained from the hydroformylation reaction zone in a distillation zone to separate butyraldehyde from the catalyst solution, and recycling the residual catalyst solution from the distillation zone to the hydroformylation reaction zone, the improvement which comprises, prior to recycling the residual catalyst solution to the hydroformulation zone, contacting at least a part of the residual catalyst solution with carbon dioxide at a partial pressure of carbon dioxide of about 5 to 100 kg/cm$^2$ and a temperature of about 60° to 200° C.

11. In a process for producing an aldehyde including the steps of supplying to a hydroformylation reaction zone an olefin selected from the group consisting of ethylene, propylene, butene and hexene, carbon monoxide and hydrogen together with a catalyst solution consisting essentially of a solvent and a rhodium-tertiary phosphine complex catalyst dissolved therein to form an aldehyde, distilling the reaction mixture obtained from the hydroformylation reaction zone and containing the aldehyde formed in a distillation zone to separate the aldehyde from the catalyst solution, and recycling the catalyst solution from the distillation zone to the hydroformylation reaction zone, the improvement which comprises contacting at least a part of the catalyst solution with carbon dioxide having the partial pressure higher than about 1 Kg/cm$^2$ at a temperature of about 60° to 200° C in the recycling system for the catalyst solution.

12. The process as claimed in claim 11, wherein the carbon dioxide partial pressure is about 1 to 100 Kg/cm$^2$.

13. The process as claimed in claim 11, wherein said tertiary phosphine of the complex catalyst is a triarylphosphine.

14. The process as claimed in claim 11, wherein said olefin is propylene.

15. The process as claimed in claim 11, wherein said olefin is ethylene.

16. The process as claimed in claim 11, wherein the molar ratio of hydrogen to carbon monoxide supplied to the hydroformylation reaction zone is about 1:3 to 7:1.

17. The process as claimed in claim 11, wherein the reaction temperature in the hydroformylation reaction zone is about 50° to 200° C.

18. The process as claimed in claim 11, wherein the concentration of the rhodium-tertiary phosphine complex in the catalyst solution supplied to the hydroformylation reaction zone is about 0.1 to 500 mg. per liter of the solvent calculated as atomic rhodium.

* * * * *